United States Patent
Talmor

[19]
[11] Patent Number: 5,851,181
[45] Date of Patent: Dec. 22, 1998

[54] APPARATUS FOR SIMULTANEOUSLY VIEWING AND SPECTRALLY ANALYZING A PORTION OF SKIN

[75] Inventor: Eli T. Talmor, Haifa, Israel

[73] Assignee: ESC Medical Systems Ltd., Yokneam, Israel

[21] Appl. No.: 708,080

[22] Filed: Aug. 30, 1996

[51] Int. Cl.⁶ .................................................. A61B 5/00
[52] U.S. Cl. ......................... 600/407; 600/473; 600/476
[58] Field of Search .................................. 128/633, 634, 128/664–666, 653.1; 600/473, 475–479, 407, 310, 317, 342

[56] References Cited

U.S. PATENT DOCUMENTS

| | | | |
|---|---|---|---|
| 4,336,809 | 6/1982 | Clark | 128/665 |
| 4,768,513 | 9/1988 | Suzuki | 128/634 |
| 5,293,872 | 3/1994 | Alfano et al. | 128/664 |
| 5,363,854 | 11/1994 | Martens et al | 128/665 |
| 5,383,467 | 1/1995 | Auer et al. | 128/665 |
| 5,608,520 | 3/1997 | Fleming | 128/633 |

OTHER PUBLICATIONS

Laser Spectroscopy in Medical Diagnostics, Andersson–Engels, et al., Chapter 24, pp. 387–417.

Optical Biopsy —Detecting Cancer With Light, Katz, et al., Hot Topics, Leos Newsletter, pp. 6–7, Feb. 1996.

*Primary Examiner*—Ruth S. Smith
*Attorney, Agent, or Firm*—Friedman Siegelbaum LLP

[57] ABSTRACT

A monitoring apparatus for monitoring an image of a treatment site and the spectral emissions from a portion of that region is provided. A CCD camera and spectrometer coupled to a housing can be directed toward an opening in the housing. This opening can be placed near a treatment site so that an image of the treatment site and a spectral measurement of the treatment site can be measured at the same time.

5 Claims, 5 Drawing Sheets ered to the housing through the opening. At least one lens may be provided to focus light entering the housing into the second end of the optical fiber. A window may be provided that is disposed across the opening in the field of
APPARATUS FOR SIMULTANEOUSLY VIEWING AND SPECTRALLY ANALYZING A PORTION OF SKIN

FIELD OF THE INVENTION

This invention relates generally to an apparatus for simultaneously viewing and spectrally analyzing a portion of skin. More particularly, it is directed to a computer-aided system for monitoring a spectral output of the skin while simultaneously viewing the area of the skin that is analyzed.

BACKGROUND OF THE INVENTION

Electromagnetic radiation is used to treat a variety of skin disorders, such as vascular and pigmented lesions, tumors, hair removal, skin rejuvenation, psoriasis, among others. This radiation is typically applied to the surface of the skin from a variety of radiation sources, such as lasers that emit coherent light, flash lamps or arc lamps emitting incoherent light and microwave radiation sources, among others. Whatever the source of electromagnetic radiation, in order to provide treatment without damaging the epidermis and surrounding tissue, careful consideration must be given to the problem of monitoring the course of treatment to minimize tissue damage, and to optimize treatment.

One method of treatment is called photo dynamic therapy (PDT) and uses a combination of light and chemicals to treat a variety of solid tumors, including skin cancers, and cancers of the internal organs, such as colon, vagina, bladder and other cancers. The PDT treatment is based on a systemic or topical application of a tumor-localizing photosensitizing agent, such as porphyrin, aminolevulinic acid (ALA), phtalocyanin, chlorine, etc., which after illumination and excitation with light in the presence of oxygen, give rise to highly reactive and cytotoxic single molecular oxygen which causes tumor regression. Typical absorption spectra of these chemicals are shown in FIG. 1.

During PDT treatment, light should be applied to the tumor until the photosensitizer agent is consumed by the beneficial chemical reaction. Once this reaction is complete and the agent is consumed, any additional light applied to the tumor may have little value. Termination of the treatment before the agent is consumed is even worse, since this may leave tumor residuals. To prevent this, some PDT operators have used a spectrometer to sense the presence or absence of the photosensitizing agent. By measuring light emitted by a photosensitizing agent in the skin during treatment and analyzing its spectrum, an operator may easily be able to tell whether any photosensitizing agent still exists at the treatment site. In the past, measuring the radiation emitted from the treatment site has been difficult to coordinate with the treatment itself. To measure the radiation from the photosensitizing agent at the treatment site, the light source used to stimulate the photosensitivity agent was removed from the proximity of the treatment site and a spectrometer was placed in proximity to the treatment site. This process was repeated each time the spectral emissions from the treatment site was checked until the photosensitizing agent was consumed. To provide for consistent treatment, the light source should have been replaced back at the identical spot from which it was removed to apply light to the identical area. This often did not happen, however. Each time the light source was replaced, it was often replaced at a slightly different location. In this manner, the light source "migrates" across the treatment site causing irregular and nonhomogeneous treatment of the tumor.

Another problem with current PDT treatment methods is the difficulty in accurately orienting the light source with respect to the treatment site. Typically, the light source obscures treatment site, and prevents the light source from being accurately positioned with respect to the treatment site, and, in the event that a larger area is treated, prevents the light source from being relocated to an adjacent area of the treatment site without leaving an untreated gap, or without overlapping an area that has already been treated, and thus treating an area twice, unnecessarily.

Another application using a combination of light and chemicals is called photo dynamic diagnostics (PDD). In this application, detection of the chemical in the tissue is used for tumor diagnosis, since chemical concentrations in the tumor are much higher than in healthy tissue. In this application, it is advantageous to view the tumor to determine its borders, as well as measure the spectrum of fluorescence of the chemicals to provide positive identification of the chemical signature. Applying light to the treatment site while the chemical fluorescence is monitored enhances the chemical's fluorescence and thereby provides a superior spectral analysis. As with PDT, this is awkward, since both a light source and a spectrometer must be disposed adjacent to the treatment area simultaneously.

The present invention advantageously provides a device that can remotely monitor the treatment site without requiring removal of a treatment or monitoring light source. A further advantage of this invention is that it allows treatment of the treatment site without requiring the light source to be moved while spectral emissions from the treatment site are measured. It is yet another advantage of this invention that it provides simultaneous light stimulation and spectrum monitoring of radiation from a treatment site to determine the limits of a tumor.

SUMMARY OF THE PRESENT INVENTION

A monitoring apparatus is provided that has a housing containing a camera and a spectrometer, both directed to an opening in the housing that is disposed next to an area to be treated. The camera provides an image of the treatment site and the spectrometer provides a spectrum of the emissions from the same treatment site. A computer takes the signal from the camera and from the spectrometer and displays the camera image of the treatment site on a computer display together with the spectral distribution of emissions from the treatment site. Thus, both the image (typically enlarged) and the spectrum of the treatment site can be viewed together. The housing may also be coupled to a light source for treating that portion of the treatment site viewed by the camera. Thus, an operator may simultaneously treat, view, and spectrally monitor the treatment site as the treatment proceeds. The image, as well as the spectrum information provided by the computer may be saved to make a permanent record of the treatment.

The present invention is directed to a special monitoring apparatus including a housing having an opening adapted to be disposed adjacent to a portion of a treatment site, a camera coupled to the housing to view the opening, and a spectrometer optically coupled to the housing and disposed to sense radiation entering the housing at the opening. The spectrometer may include an optical bench disposed remotely from the housing and coupled to a first end of an optical fiber, wherein the second end of the optical fiber is coupled to the housing and disposed such that it receives radiation entering the housing through the opening. At least one lens may be provided to focus light entering the housing into the second end of the optical fiber. A window may be provided that is disposed across the opening in the field of view of the camera and between the camera and the opening. The second end may be coupled to this window such that the second end is disposed in a field of view of the camera. A treatment or monitoring light source may be coupled to the housing and disposed so that light emitted from the light source is directed toward the opening of the housing. The light source may include an arc lamp disposed remotely from the housing and a light guide having a first and second end, wherein the first end is coupled to the arc lamp to receive treatment light emitted by the arc lamp, and wherein the second end is coupled to the housing and adapted to transmit the treatment light toward the opening. The apparatus may also include a computer coupled to the camera to receive images transmitted from the camera and coupled to the spectrometer to receive signals indicative of the spectrum of radiation entering the housing from the opening. The apparatus may also include a computer display coupled to the computer and adapted to display a spectral distribution calculated by the computer from the spectral signal and transmitted by the computer to the display as well as an image received by the computer from the camera. The display may be adapted to display both an image and a spectral distribution simultaneously.

Other principal features and advantages of the invention will become apparent to those skilled in the art upon review of the following drawings, the detailed description and the appended claims.

Figure 1:
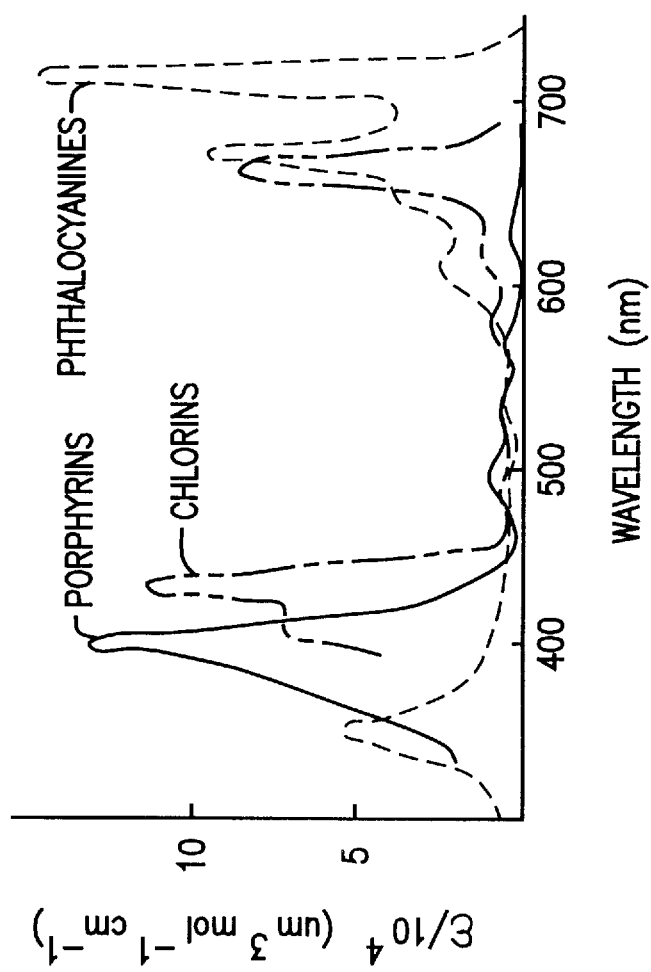
FIG. 1 is a spectral absorption spectra of photosensitizing agents for PDT.

Before explaining at least one embodiment of the invention in detail it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION OF THE PREFERRED EMBODIMENTS

Figure 2:
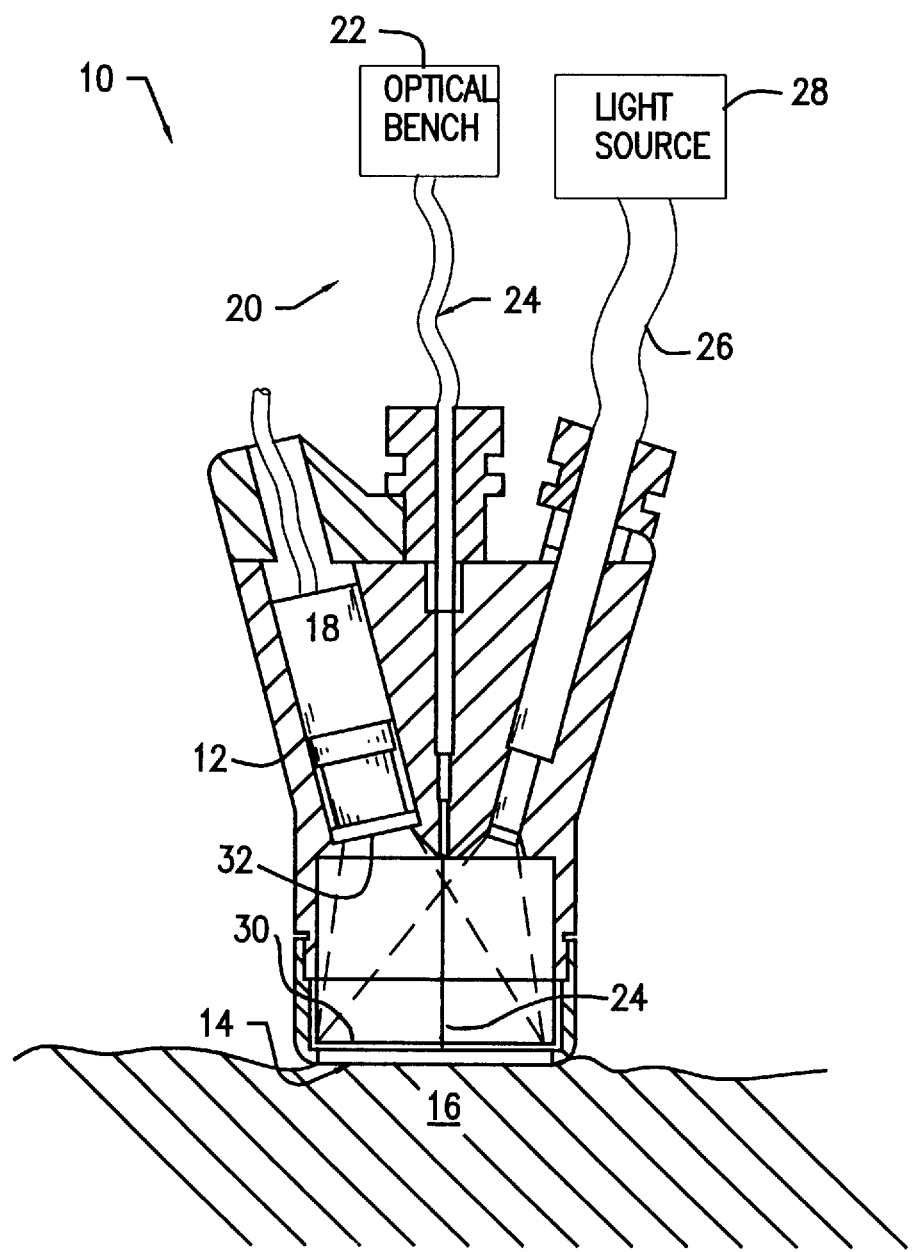
FIG. 2 is a partial cross-sectional diagram of a monitoring apparatus in accordance with the present invention.

Regarding FIG. 2, a monitoring apparatus 10 is shown having a housing 12, with an opening 14 disposed against a treatment site 16 which is typically human skin. Housing 12 includes a camera 18 coupled to the housing and oriented to receive light entering the housing from opening 14. In this case, since the opening is disposed adjacent to treatment site 16, the camera receives images of the treatment site that is adjacent to opening 14. Housing 12 preferably provides an internal chamber that blocks out external light when opening 14 is placed against a treatment site on the skin, thus reducing interference from other devices, such as fluorescent lights.

Spectrometer 20 includes optical bench 22 disposed away from housing 12, and light guide 24 (typically an optical fiber or fiber bundle) coupled to housing 12 and optical bench 22 to direct radiation entering housing 12 through opening 14 into optical bench 22. Spectrometer 20 is preferably of the type known in the art as an optical multichannel analyzer (OMA). The advantage to using an OMA is that rapid, nearly real-time spectral measurements are possible. OMA spectral range is generally 400 to 1000 nanometers, although a spectrometer 20 providing a narrower spectral range of 570 to 770 nanometers can be employed for fluorescence monitoring.

A light guide 26 is coupled to the housing to transmit light from light source 28 into the housing and toward the opening 14. The light is preferably generated either by a laser or a flashlamp, both of which have emissive qualities particularly suited to being coupled to housing 12. In this manner light for treatment is sent to treatment site 16.

Light source 28 is preferably a high intensity light source such as a xenon or mercury arc lamp. It may have one or more filters, such as a violet filter passing wavelengths in the range of 400 to 450 nanometers or a green filter passing wavelengths in the range of 505 to 590 nanometers. These wavelengths are particularly useful when using the system in PDT and PDD, since these are the frequencies that cause common photosensitizing chemicals to fluoresce significantly.

A window 30 is provided that extends across the opening 14. Light guide 24 is coupled to the window, preferably in the field of view of the camera such that an image produced by the camera indicates the point at which the light guide is coupled to the window. The light guide preferably receives light emitted from a spot on the treatment site measuring between 1 and 10 mm$^2$. The window transmits light from the light source out of the housing and onto the treatment site. It also transmits light emitted from the treatment site into the housing and thence into the camera. The optical fiber preferably extends through the window such that it receives light emitted directly from the treatment site without having to pass through the window. The inner and outer surfaces of the window preferably have an anti-reflective coating to attenuate any reflections internal to the housing from entering the camera. Window 30 is preferably recessed within opening 14 of housing 12. The depth of this recess is preferably between 3 and 10 mm.

The camera is an electronic camera, preferably a color or black-and-white CCD camera. The camera is disposed to provide an image that includes from 1 to 100 cm$^2$ of the treatment site. More preferably, the image includes from 10 to 40 cm$^2$ of the treatment site. Most preferably, the image includes from 15 to 25 cm$^2$ of the treatment site. It may include a filter 32 disposed in the camera's optical path to block particular frequencies of light, such as the frequencies emitted by the light source. For typical PDT therapies, the filter should transmit light in the range of 570 to 770 mm. This is of particular value when the camera is used to sense frequencies of light emitted by fluorescing photosensitizing agents (that typically emit in the 570–770 nm range) in response to the light emitted by the light source. When the frequencies emitted by the light source are different from the frequencies emitted by the photosensitizing agents, a filter that eliminates the light source frequencies can by reducing or eliminating the intense light source frequencies provide enhanced camera perception of the fluorescing frequencies. The camera is best disposed at an angle of between 10 and 20 degrees of a perpendicular which extends from the surface of a treatment site (e.g. a plane extending across the opening).

In FIG. 2, a portion of light guide 24 is disposed in the optical path of the camera, and thus tends to partially obstruct the camera's view. While this obstruction cannot be eliminated in the FIG. 2 embodiment, it may be significantly reduced by providing a light guide 24 having a diameter of between 0.1 and 1 mm. A light guide of this diameter provides a minimum of interference with the camera's image, while also conducting sufficient light from a range of 1 to 10 mm$^2$ area of the treatment site to provide a good spectral analysis of the treatment site.

Opening 14 in this embodiment is substantially circular, which allows the light source to illuminate and the camera to monitor substantially the same treatment area. A second preferred opening is an elliptical opening where a line drawn through the major axis of the ellipse lies substantially in the same plane as a line defining the central axis of the camera optics or a line defining the central axis of any light emitted by the light source, or both.

Figure 3:
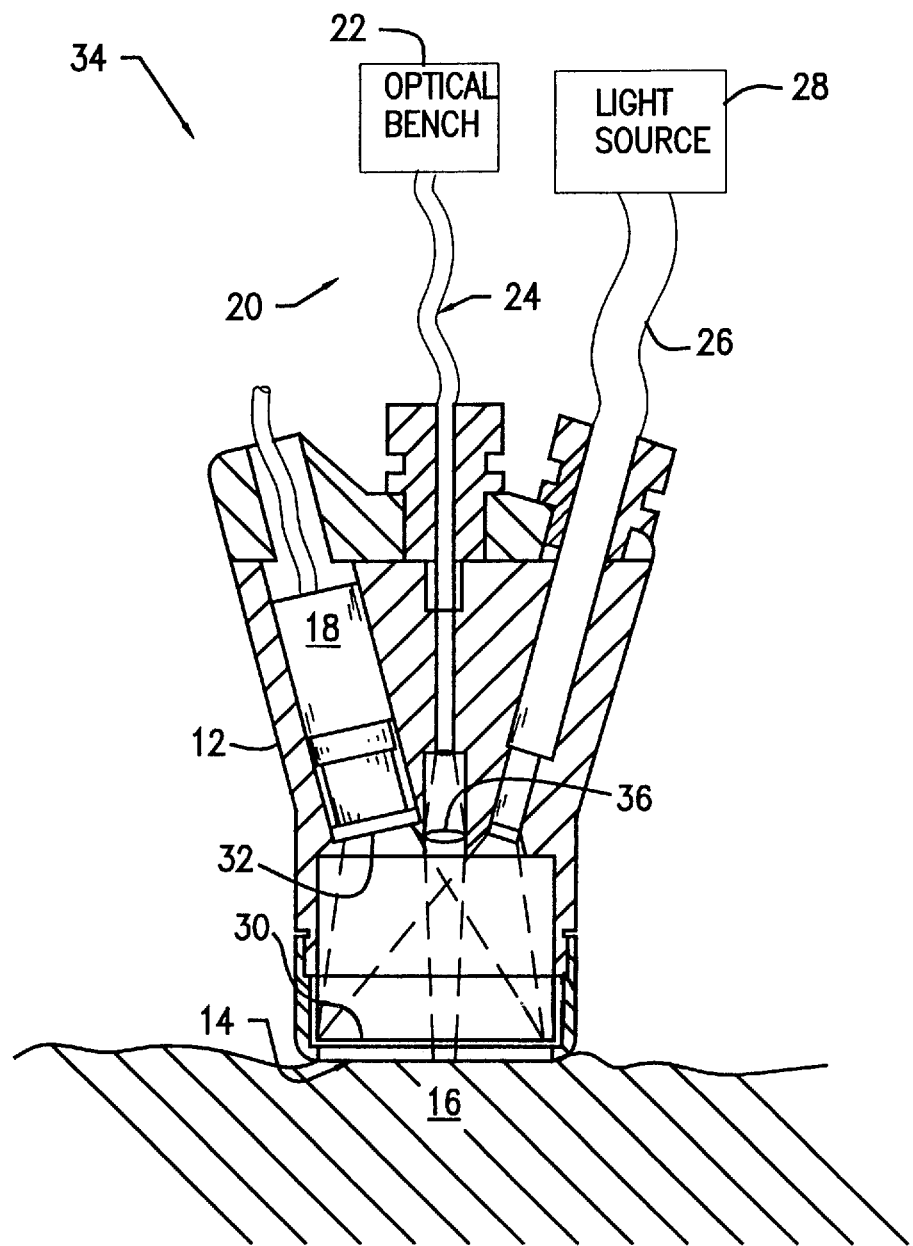
FIG. 3 is a partial cross-sectional view of a second monitoring apparatus.

In FIG. 3, a monitoring apparatus 34 is shown similar to that of FIG. 2. In this embodiment, however, light guide 24 is not coupled to window 30. Lens 36 is optically coupled to light guide 24 to focus light received into the opening onto light guide 24. Lens 36 is adapted to focus light emitted from an area of the treatment site measuring preferably between 1 and 10 mm$^2$, similar to that discussed above. Lens 36 is preferably fixed to the housing, adjacent to the camera.

Figure 4:
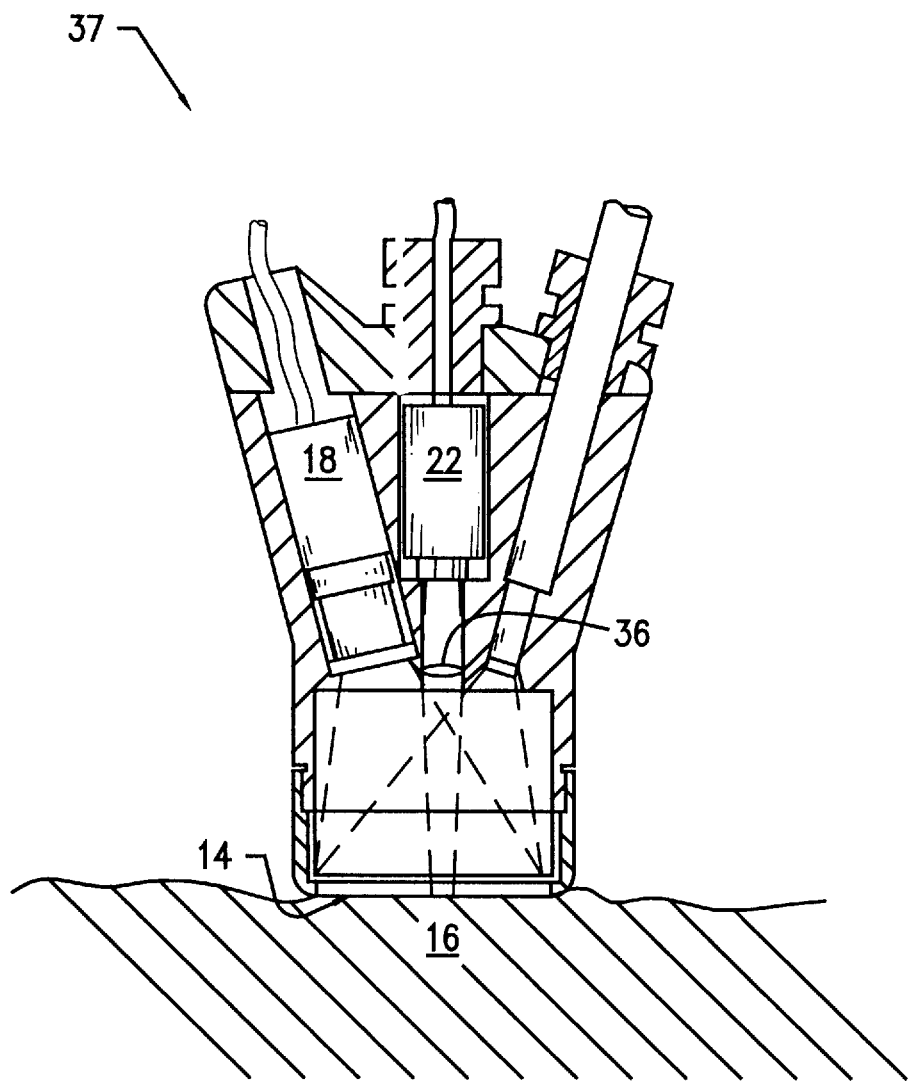
FIG. 4 is a partial cross-sectional view of a third monitoring apparatus.

In FIG. 4, a monitoring apparatus 37 is shown similar to that of FIG. 2. In this embodiment, however, optical bench is disposed in the housing itself, eliminating the need for optically coupling the optical bench via an extended light guide, and thus eliminating the resultant attenuation. As with the embodiment of FIG. 3, the optical bench in this embodiment includes a lens 36 adapted to focus light emitted from a treatment site measuring preferably between 1 and 10 mm$^2$.

Figure 5:
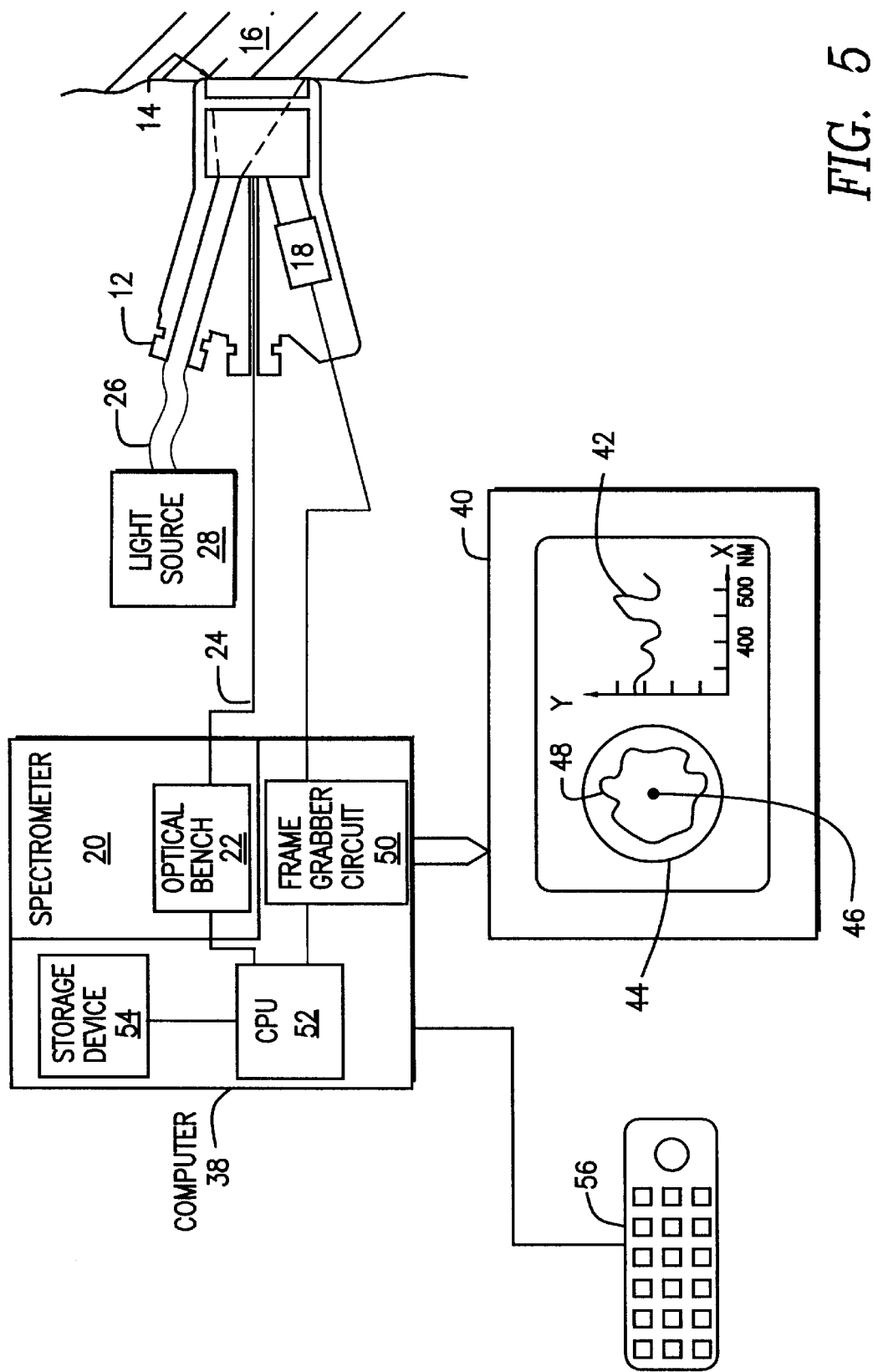
FIG. 5 is a block diagram of a monitoring apparatus including a computer and display.

FIG. 5 discloses a monitoring apparatus similar to any of the above embodiments and further including a computer 38 coupled to spectrometer 20, camera 18 and computer display 40. Computer 38 receives signals from spectrometer 20 indicative of the spectrum of light received by spectrometer 20. These signals are processed by the computer which then transmits an electrical signal to display 40 causing display 40 to generate a representation of the spectrum 42 on the display. In the preferred embodiment, the spectrum is shown in graphical form as a function on display 40, in which the horizontal or X-axis indicates the frequency or wavelength of light received by the spectrometer, and the vertical or Y-axis indicates a value indicative of the relative intensity of light received by the spectrometer.

The computer also transmits signals to display 40 indicative of the images received by camera 18. Display 40 is preferably adapted to produce these sequential images of the treatment site concurrently with the spectrum. One such image (item 44) is shown in FIG. 5. Thus, an operator of the system can monitor the spectral emissions of the treatment site simultaneously with an image of the treatment site. Preferably, these images and spectrums are displayed in real time, as the light from the treatment site is received by the spectrometer and the camera. This mode of operation has a synergistic effect, allowing the operator of the system to provide and monitor treatment by viewing a computer display rather than by viewing the treatment site itself. All the information required to determine where and when to move housing with respect to the treatment site is provided on the screen.

Image 44 also indicates the point at which the spectrum 42 has been measured. At the point where light guide 24 (FIG. 2) is coupled to window 30 (FIG. 2) will appear in each camera image as a small spot or shadow. In this manner, the operator will not only be able to determine the spectrum of radiation emitted from the treatment site, but will be able to identify in the camera image on display 40 the spot 46 where that measurement was taken. Alternatively, in an embodiment where the light guide is not coupled to the window, such as that shown in FIGS. 3 or 4, a computer generated mark may be transmitted to the display to appear in each image at the place where the spectrometer measured the spectrum. Camera 18 preferably displays a larger portion of the treatment site than is sensed by spectrometer 20. In this manner, the operator while watching the display can view a large portion of treatment site 16, pan housing 12 about the treatment site, and clearly identify various portions of affected region 48 of treatment site 16 and their corresponding spectral behavior. This allows the operator to create in her own mind an overall image of the spectral distribution across affected region 48.

Camera 18 is coupled to a frame-grabber circuit 50 that retrieves successive images of the treatment site from camera 18 under control of the central processing unit 52. The frame-grabber circuit is coupled to central processing unit 52, which can be programmed to further process the image. By actuating keys, trackball, touchpad, joystick or other user input device (shown here as item 56) coupled to central processing unit 52, the operator can select particular images, spectra corresponding to those images, or both, for storage in storage device 54, coupled to central processing unit 52. In this manner, a treatment can be documented and saved for future reference, or for comparison with images of the same treatment site to be taken in the future in order to determine the effectiveness of treatment.

Spectrometer 20 is here shown with optical bench 22 disposed within computer 38 and coupled to housing 12 via light guide 24. Alternatively, the embodiment of FIG. 4 can be employed, and the optical bench can be disposed remotely from the computer or within the housing itself. This prevents or reduces light losses that may occur due to the attenuation caused by light guide 24.

Thus, it should be apparent that there has been provided in accordance with the present invention a method and apparatus for simultaneously viewing and spectrally analyzing the portion of the skin that fully satisfies the objectives and advantages set forth above. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The embodiments of the invention in which an exclusive property or privilege is claimed are defined as follows:

1. A spectral monitoring apparatus comprising:
    a housing having an opening adapted to be disposed adjacent to a portion of a treatment site;
    a camera coupled to the housing to view the opening; and
    a spectrometer optically coupled to the housing and disposed to sense radiation entering the housing at the opening;
    wherein the spectrometer includes an optical bench disposed remotely from the housing and coupled to a first end of an optical fiber, wherein a second end of the optical fiber is coupled to the housing and disposed such that it receives radiation entering the housing through the opening;
    the spectral monitoring apparatus further comprising a window coupled to the housing and disposed across the opening;

wherein the second end of the optical fiber is coupled to the window such that the second end is disposed in a field of view of the camera.

2. A spectral monitoring apparatus comprising:

a housing having an opening adapted to be disposed adjacent to a portion of a treatment site;

a camera coupled to the housing to view the opening; and a spectrometer optically coupled to the housing and disposed to sense radiation entering the housing at the opening;

wherein a field of view of the camera includes between 10 and 40 square centimeters at the opening of the housing.

3. The spectral monitoring apparatus of claim 2, wherein a field of view of the camera includes between 15 and 25 square centimeters at the opening of the housing.

4. A spectral monitoring apparatus comprising:

a housing having an opening adapted to be disposed adjacent to a portion of a treatment site;

a camera coupled to the housing to view the opening; and a spectrometer optically coupled to the housing and disposed to sense radiation entering the housing at the opening;

further comprising a light source optically coupled to the housing and disposed so that light emitted from the light source is directed toward the opening of the housing;

and further comprising a filter disposed between the camera and the opening of the housing to filter out light emitted by the light source;

wherein the filter passes wavelengths of light emitted by fluorescing photosensitizing chemicals;

wherein further the filter passes wavelengths between 570 and 770 nanometers;

the light source further including a second filter passing wavelengths that are not passed by the filter disposed between the camera and the opening;

wherein the second filter passes wavelengths of between 505 and 590 nanometers.

5. A spectral monitoring apparatus comprising:

a housing having an opening adapted to be disposed adjacent to a portion of a treatment site;

a camera coupled to the housing to view the opening; and a spectrometer optically coupled to the housing and disposed to sense radiation entering the housing at the opening;

further comprising a light source optically coupled to the housing and disposed so that light emitted from the light source is directed toward the opening of the housing;

further comprising a window coupled to the housing and disposed across the opening wherein the light source, the housing, the camera, and the window are optically disposed such that light transmitted by the light source traverses the housing, passes through the window, causes a photo-sensitizing chemical to fluoresce and emit light at a fluorescent wavelength, and wherein such light at a fluorescent wavelength is transmitted back through the window and into the camera.

* * * * *